United States Patent [19]

Ferland et al.

[11] 4,140,779
[45] Feb. 20, 1979

[54] ARYLOXY PROPYLDIAMINES

[75] Inventors: Jean-Marie Ferland, St. Laurent; Réal R. Laliberte, Chomedey; Wilbur Lippmann, Montreal; Thomas A. Pugsley, Kirkland, all of Canada

[73] Assignee: Ayerst, McKenna and Harrison Limited, Montreal, Canada

[21] Appl. No.: 687,850

[22] Filed: May 19, 1976

[51] Int. Cl.$^2$ .................. C07D 295/12; A61K 31/455
[52] U.S. Cl. ........................... 424/267; 424/248.56; 424/250; 424/274; 424/330; 546/206; 546/191; 260/326.5 C; 260/349; 260/570.7; 544/79; 544/121; 544/129; 544/141; 544/357; 544/372; 544/398
[58] Field of Search .................. 260/247.5 R, 268 BC, 260/293.62, 326.5 L, 570.7, 349, 326.5 C; 424/248.56, 250, 267, 274, 330; 544/162, 398

[56] References Cited
PUBLICATIONS

Dauksas et al., Zh. Vscs. Khim. Obshchestva im. D. I. Meadeleeva, 9(3), pp. 352–354, (1964); Chem. Abstracts 61:6942c, (1964).
Cram et al., "Organic Chemistry", McGraw–Hill, New York, pp. 255 and 257.

Primary Examiner—Henry R. Jiles
Assistant Examiner—R. W. Ramsuer
Attorney, Agent, or Firm—Adley F. Mandel

[57] ABSTRACT

Disclosed herein are compounds of the formula

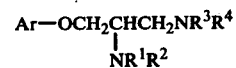

in which Ar is 1-naphthyl; $R^1$ and $R^2$ are either the same or different selected from the group consisting of hydrogen or lower alkyl, or $R^1$ and $R^2$ together with the nitrogen atom to which they are joined form a heterocyclic amine radical selected from the group consisting of 1-pyrrolidinyl, piperidine, morpholine and 4-(lower alkyl)-1-piperazinyl; and $R^3$ and $R^4$ are either the same or different selected from the group consisting of hydrogen or lower alkyl, or $R^3$ and $R^4$ together with the nitrogen to which they are joined represent a heterocyclic amine radical selected from the group consisting of 1-pyrrolidinyl, piperidino, morpholino and 4-(lower alkyl)-1-piperazinyl; or a therapeutically acceptable acid addition salt thereof. The compounds are antidepressant agents and methods for their preparation and use also are disclosed.

19 Claims, No Drawings

ARYLOXY PROPYLDIAMINES

BACKGROUND OF THE INVENTION (a) Field of the Invention

This invention relates to aryloxy propyldiamines having antidepressant activity, to a process for their preparation, to intermediates used for the process, and to formulations and a method of use for these aryloxy propyldiamines.

(b) Prior Art

During the last few decades, psychotherapy has become more effective due to the adjunct use of new central nervous system agents, in particular, the use of tranquilizers and antidepressants. As a consequence, the development of new and useful agents for psychotherapy has been diligently pursued, and the finding of a potent, well tolerated agent is noteworthy indeed.

The present invention dicloses a group of antidepressant agents having these attributes. The agents are aryloxy propyldiamines. A number of aryloxy propyldiamines having a stimulating effect on the central nervous system have been reported by V. Dauksas and L. Pikunaite, Zh. Vses. Khim. Obshchestva im. D. I. Mendeleeva, 9, 352 (1964); Chem. Abstr, 61, 6942c (1964). The compounds of the present invention are distinguished readily from the prior art compounds by having a different aryloxy substituent and a different pharmacological profile.

SUMMARY OF THE INVENTION

The compounds of this invention are represented by formula 1

in which Ar is 1-naphthyl; $R^1$ and $R^2$ are either the same or different selected from the group consisting of hydrogen or lower alkyl, or $R^1$ and $R^2$ together with the nitrogen atom to which they are joined form a heterocyclic amine radical selected from the group consisting of 1-pyrrolidinyl, piperidino, morpholino and 4-(lower alkyl)-1-piperazinyl; and $R^3$ and $R^4$ are either the same or different selected from the group consisting of hydrogen or lower alkyl, or $R^3$ and $R^4$ together with the nitrogen to which they are joined represent a heterocyclic amine radical selected from the group consisting of 1-pyrrolidinyl, piperidino, morpholino and 4-(lower alkyl)-1-piperazinyl; or a therapeutically acceptable acid addition salt thereof.

Pharmaceutical compositions comprising the compound of formula I, or a therapeutically acceptable acid addition salt thereof, and a pharmaceutically acceptable carrier are included within the scope of this invention.

Also included is a method for alleviating the symptoms of depression in mammals by administering to said animals an antidepressant effective amount of the compound of formula I, or a therapeutically acceptable salt thereof.

DETAILS OF THE INVENTION

The term "lower alkyl" as sused herein contemplates straight chain alkyl radicals containing from one to six carbon atoms and branched chain alkyl radicals containing three to four carbon atoms and includes methyl, ethyl, propyl, isopropyl, butyl, isobutyl, hexyl and the like.

The compounds of formula I are capable of forming acid addition salts with therapeutically acceptable acids. Such acid addition salts are included within the scope of this invention.

The acid addition salts are prepared by reacting the corresponding base form of the compounds of formula 1 with at least one equivalent, or preferably with an excess of the appropriate acid in an organic solvent, for example, diethyl ether or an ethanol-diethyl ether mixture. It should be noted that both mono- and di-acid addition salts can be obtained depending on the number of equivalents of the acid used and the solubility of a particular acid addition salt in a particular solvent. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formula 1 which result from asymmetric centers contained therein.

Individual optical isomers, which might be separated by fractional crystallization of the diastereoisomeric salts thereof, for instance, salts with d- or l-tartaric acid or D-(+)-α-bromocamphor sulfonic acid, are also included.

The antidepressant activity of the compounds of formula 1 and their acid addition salts with pharmaceutically acceptable acids is demonstrated in standard pharmacologic tests such as, for example, the tests described by F. Hafliger and V. Burchkhart in "Psychopharmacological Agents", M. Gordon, Ed., Academic Press, New York and London, 1964, pp. 75 -83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 100 mg/kg.

The antidepressant activity of the compounds of the formula 1 is also demonstrated by the method of D. F. Bogdanski, et al., J. Pharmacol, Exp. Ther., 122, 182 (1958) which measures the effect of the test compound of the 5-hydroxytryptophan (5-HTP)-induced syndrome. In this test the degree of intensity of the 5-HTP-induced syndrome, i.e., extension and abduction of hindlimbs, lordosis, tremors, head movements and excitation, following the administration of the test compound to Swiss albino mice, is indicated by a scale ranging from +1 (weak effect) to +4 (very strong effect). A positive score in the test is indicative of antidepressant agents having desirable mood elevation properties, see A. Carlosson, et al., Eur. J. Pharmacol., 5, 357 (1969). Several of the preferred compounds, for example β-[(1-naphthyloxy)methyl]-1-piperidineethanamine hydrochloride, produces a significant effect (+1 to +4) on the 5-HTP induced syndrome at doses of 6.25 to 25 mg/kg, i.p., when administered to mice (five per group)

30 minutes prior to the 5-HTP injection (300 mg/kg, i.p.).

The following table illustrates further a comparative study β-[(1-naphthyloxy)methyl]-1-piperidineethanamine hydrochloride, imipramine hydrochloride and desimipramine hydrochloride in the potentiation of the 5-HTP-syndrome test.

| Compound | Dose(mg/kg,i.p.) | Behavioral Score |
|---|---|---|
| saline | — | 0 |
| β-[(1-naphthyloxy)methyl]-1-piperidineethanamine hydrochloride (Example 4) | 25 | +4 |
|  | 12.5 | +3 |
|  | 6.25 | +1 |
| Imipramine hydrochloride | 25 | +3 |
|  | 12.5 | +2 |
|  | 6.25 | +1 |
| desimipramine hydrochloride | 25 | +1 |

The 5-HTP-syndrome test can also be employed to demonstrate the superiority of the compounds of formula 1 over corresponding analogs in which the 1-naphthyl group is replaced by a phenyl group (cf. Dauksas and Pikunaite, cited above). For example, under the testing conditions noted above in which β-[(1-naphthyloxy)methyl]-1-piperidineethanamine hydrochloride, is active, the corresponding phenyl analog, β-(phenoxymethyl)-1-piperidineethanamine hydrochloride, is inactive.

When the compounds of formula 1 are used as antidepressants in mammals, e.g. rats and mice, they may be used alone or in combination with pharmacologically acceptable carriers, the proportion of which is determined by the solubility and chemical nature of the compound, chosen route of administration and standard biological practice. For example, they are administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.1 mg to about 100 mg/kg per day, although as aforementioned variations will occur. However, a dosage level that is in the range of from about 0.5 mg to about 50 mg/kg per day is most desirably employed in order to achieve effective results.

The compounds of formula 1 in which Ar, $R^1$, $R^2$, $R^3$ and $R^4$ are as defined herein are prepared by a process represented by the following flow diagram.

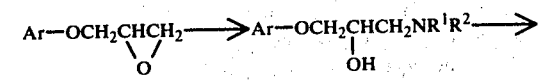

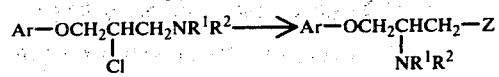

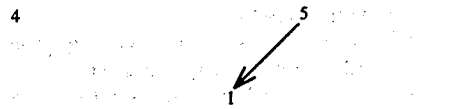

With reference to the flow diagram, the starting material of formula 2 in which Ar is 1-naphthyl, 1,2-epoxy-3-(1-naphthyloxy)propane, is described by A. F. Crowther and L. H. Smith, J. Med. Chem., 11, 1009 (1968), and references therein.

With reference to the flow diagram, the compounds of formula 1 in which Ar, $R^1$, $R^2$, $R^3$ and $R^4$ are as defined herein are prepared by a process comprising:

reacting the starting material of formula 2 with an amine of formula $NHR^1R^2$ in which $R^1$ and $R^2$ are as defined herein to obtain the corresponding β-hydroxypropylamine of formula 3 in which Ar, $R^1$ and $R^2$ are as defined herein; reacting the last-named compound with p-toluenesulfonic acid chloride or thionyl chloride to obtain the corresponding β-chloropropylamine of formula 4, and thereafter either reacting the β-chloropropylamine of formula 4 with sodium or potassium azide to obtain the corresponding compound of formula 5 in which Z is the azide radical (—$N_3$) and reducing the latter compound either with hydrogen in the presence of a suitable catalyst or with a suitable complex metal hydride to obtain the corresponding compound of formula 1 in which Ar, $R^1$ and $R^2$ are as defined herein and $R^3$ and $R^4$ each are hydrogen; or reacting said β-chloropropylamine with an appropriate amine of formula $NHR^3R^4$ in which $R^3$ is hydrogen or lower alkyl and $R^4$ is lower alkyl, or $R^3$ and $R^4$ together with the nitrogen atom to which they are joined form a heterocyclic amine radical as defined herein, to give the corresponding compound of formula 5 in which Z is $NR^3R^4$ in which $R^3$ is hydrogen or lower alkyl and $R^4$ is lower alkyl, or $R^3$ and $R^4$ together with the nitrogen atom to which they are joined form a heterocyclic amine radical as defined herein, said last-named compound being identical to the compound of formula 1 in which Ar, $R^1$ and $R^2$ are as defined herein, and $R^3$ is hydrogen or lower alkyl, or $R^3$ and $R^4$ together with the nitrogen atom to which they are joined form a heterocyclic amine radical as defined herein.

More specifically, convenient conditions for converting the starting material of formula 2 to the corresponding hydroxypropylamine of formula 3 include reacting the starting material of formula 2 with about one to two molar equivalents of the appropriate amine of formula $NHR^1R^2$. An inert solvent, for example, diethyl ether, methanol or tetrahydrofuran, may be employed for the reaction. Usual reaction temperatures and times are from 0 to 100° C. for ten minutes to 24 hours.

Subsequent transformation of the hydroxypropylamine of formula 3 to the corresponding β-chloropropylamine is conveniently effected by reacting in an inert organic solvent the hydroxypropylamine with about one molar equivalent of tosyl chloride or thionyl chloride, tosyl chloride being preferred, at 10 to 80° C. for two to 24 hours. The reaction is preferably carried out in the presence of an excess of an organic base, for example, triethylamine or pyridine. Suitable inert organic solvents include benzene, diethyl ether or tetrahydrofuran.

In one aspect of the process of this invention, the β-chloropropylamine of formula 4 is converted to the compound of formula 5 in which Z is the azido radical by treating a solution of the β-chloropropylamine in a water-immiscible solvent with an aqueous solution of 1.0 to 1.2 molar equivalents of sodium or potassium azide. Convenient conditions include the use of dimethylformamide, acetone or methanol, temperatures ranging from 20 to 100° C. or the boiling point of the mixture and a reaction time ranging from one to six hours.

Thereafter, the compound of formula 5 in which Z is the azido radical is reduced to yield the corresponding primary amine of formula 1 in which Ar, $R^1$ and $R^2$ are as defined herein and $R^3$ and $R^4$ each is hydrogen. This reduction is effected by reacting the latter compound of formula 5 with gaseous hydrogen in the presence of a noble metal catalyst, for example, platinum, platinum oxide, palladium or palladium oxide, in a suitable inert organic solvent, for example, methanol, ethanol or dioxane. Alternatively, the reduction is effected by reaction of the compound of formula 5 with a suitable complex metal hydride. Examples of suitable complex metal hydrides are lithium aluminum hydride, lithium aluminum hydride-aluminum chloride, aluminum hydride - aluminum chloride, diborane and sodium borohydride-aluminum chloride. Lithium aluminum hydride is preferred.

It should be noted that a second product can be isolated from the aforementioned reaction producing the compound of formula 5 in which Z is the azido radical. The second product is the positional isomer of the compound of formula 5 with respect to Z and $NR^1R^2$. The positional isomer, by catalytic reduction or by reduction with a complex metal hydride, as described above, gives the corresponding compound of formula 1 in which $R^1$ and $R^2$ each are hydrogen. The structures of the first and second product are determined by nuclear magnetic resonance spectroscopy and mass spectroscopy.

In another aspect of this process, the β-chloropropylamine of formula 4 is converted to a compound of formula 5 in which Z is $NR^3R^4$ wherein $R^3$ is hydrogen or lower alkyl and $R^4$ is lower alkyl, or $R^3$ and $R^4$ together with the nitrogen atom to which they are joined form a heterocyclic amine radical as defined herein, by reacting the β-chloroporpylamine with a suitable amine of formula $NHR^3R^4$ in which $R^3$ is hydrogen or lower alkyl and $R^4$ is lower alkyl, or $R^3$ and $R^4$ together with the nitrogen atom to which they are joined form a heterocyclic amine radical as defined herein. Examples of suitable amines are methylamine, diisopropylamine, butylamine, pyrrolidine, piperidine, and the like. Convenient conditions for effecting this reaction include treating a mixture of the β-chloropropylamine with at least two molar equivalents, usually two to ten molar equivalents of the amine, with or without the use of an inert organic solvent, for example, tetrahydrofuran, diethyl ether, or benzene, as a reaction medium, at 20 to 100° C. or the boiling point of the reaction for a period of four to 24 hours. In this manner the compounds of formula 5 in which Ar, $R^1$ and $R^2$ are as defined herein and Z is $NR^3R^4$ wherein $R^3$ is hydrogen or lower alkyl and $R^4$ is lower alkyl, or $R^3$ and $R^4$ together with the nitrogen atom to which they are joined form a heterocyclic amine radical as defined herein, are obtained. The latter compounds are identical to corresponding compounds of formula 1 in which $R^3$ is hydrogen or lower alkyl and $R^4$ is lower alkyl, or $R^3$ and $R^4$ together with the nitrogen atom to which they are joined form a heterocyclic amine radical as defined herein.

In addition, the positional isomer of the latter compound with respect to Z and $NR^1R^2$ can be isolated from the preceding reaction as a second product. The second product is separated from the main product, the compound of formula 5, by conventional methods such as chromatography. The structures of the first and second product are determined by nuclear magnetic spectroscopy and mass spectroscopy.

The following examples illustrate further this invention.

EXAMPLE 1

3-(1-Pyrrolidinyl)-1-(1-naphthyloxy)-2-propanol (3; Ar = 1-naphthyl and $NR^1R^2$ = 1-pyrrolidinyl)

A solution of 1,2-epoxy-3-(1-naphthyloxy)propane (62.0 g) and the amine of formula $NHR^3R^3$, pyrrolidine (23.5 g), in methanol (250 ml) is heated at reflux for two hours. The reaction mixture is concentrated to dryness. The oily residue is crystallized from chloroform and diethyl ether by the addition of hexane to give the title compound, mp 68–70° C.

In the same manner but replacing pyrrolidine with an equivalent amount of piperidine, morpholine or N-methylpiperazine, 3-piperidino-1-(1-naphthyloxy)-2-propanol, $\gamma_{max}$-$nujol$ 3250 and 2655 cm$^{-1}$, (the corresponding hydrochloride of the latter compound has mp 189-190° C.),
3-morpholino-1-(1-naphthyloxy)-2-propanol, mp 68-70° C., and
3-(4-methyl-1-piperazinyl)-1-(1-naphthyloxy)-2-propanol, mp 73-74° C., are obtained, respctively.

In the same manner but replacing pyrrolidine with an equivalent amount of ethylamine, butylamine or diisopropylamine, 3-(ethylamino)-1-(1-naphthyloxy)-2-propanol,
3-(butylamino)-1-(1-naphthyloxy)-2-propanol, and
3-(diisopropylamino)-1-(1-naphthyloxy)-2-propanol, mp 173-174° C., after recrystallization from methanol-diethyl ether, are obtained, respectively.

EXAMPLE 2

1-{[2-Chloro-3-(1-naphthyloxy)]propyl}pyrrolidine (4; Ar = 1-naphthyl and $NR^1R^2$ = 1-pyrrolidinyl)

A solution of 3-(1-pyrrolidinyl)-1-(1-naphthyloxy)-2-propanol (56 g), described in Example 1, and tosyl chloride (43 g) in benzene (500 ml) is heated at reflux for 18 hours. The mixture is cooled, washed with dilute sodium bicarbonate and extracted with dilute hydrochloric acid. The dilute hydrochloric acid extract is washed with ether, rendered neutral with dilute sodium hydroxide and extracted with chloroform ($CHCl_3$). The $CHCl_3$ extract is dried and concentrated. The residue is subjected to chromatography using silica gel as the absorbent. Elution with diethyl ether-methanol (9:1) yields unchanged starting material. Subsequent elution with diethyl ether-methanol (7:3) yields the title compound.

In the same manner but replacing 3-(1-pyrrolidinyl)-1-(1-naphthyloxy)-2-propanol with an equivalent amount of 3-piperidino-1-(1-naphthyloxy)-2-propanol,
3-morpholino-1-(1-naphthyloxy)-2-propanol,
3-(4-methyl-1-piperazinyl)-1-(1-naphthyloxy)-2-propanol,
3-(ethylamino)-1-(1-naphthyloxy)-2-propanol,
3-(butylamino)-1-(1-naphthyloxy)-2-propanol, or
3-(diisopropylamino)-1-(1-naphthyloxy)-2-propanol,
the following β-chloropropylamines of formula 4, 1-{[2-chloro-3-(1-naphthyloxy)]propyl}piperidine, mp 45-48° C.,
1-{[2-chloro-3-(1-naphthyloxy)]propyl}morpholine, bp 158-160° C./0.02 mm/Hg,
1-{[2-chloro-3-(1-naphthyloxy)]propyl}-4-methylpiperazine,
2-chloro-N-ethyl-3-(1-naphthyloxy)propylamine,
2-chloro-N-butyl-3-(1-naphthyloxy)propylamine, and
2-chloro-N,N-diisopropyl-3-(1-naphthyloxy)propylamine, $\lambda_{max}^{EtOH}$ 319 nm ($\epsilon$ = 1850), 305 nm ($\epsilon$ = 3420), 288 nm ($\epsilon$ = 6380) and 229 nm ($\epsilon$ = 31,400), are obtained, respectively.

The hydrochloric acid addition salt of the latter compound has mp 149-152° C., after recrystallization from methanol-diethyl ether.

EXAMPLE 3

1-{[1-(Azidomethyl)-2-(1-naphthyloxy)]ethyl}pyrrolidine (5; Ar = 1-naphthyl, $NR^1R^2$ = 1-pyrrolidinyl and Z = $N_3$)

A solution of sodium azide (3.3 g) in water (15 ml) is added to a solution of 1-{[2-chloro-3-(1-naphthyloxy)]-propyl}pyrrolidine (14 g), described in Example 2, in dimethylformamide (45 ml). The mixture is heated on a steam bath for 2 hours. The mixture is extracted with diethyl ether. The extract is washed with water, dried and evaporated. The residue is subjected to chromatography on silica gel. Elution with hexane-diethyl ether (1:1) yields the title compound, nmr (CDCl₃) δ. 1.80 (m, 4H), 2.8 (m, 4H), 3.1 (m, 1H), 3.74 (d, J = 5.5, 2H), 4.32 (d, J = 5.5, 2H), 6.8 - 8.4 (m, 7H).

Continued elution with the same solvent gives the positional isomer,1-{[2-azido-3-(1-naphthyloxy)]-propyl}pyrrolidine, nmr (CDCl₃) δ 1.50 (m, 6H), 2.54 (m, 6H), 4.20 (m, 3H) and 6.70–8.50 (m, 7H).

In the same manner but replacing 1-{[2-chloro-3-(1-naphthyloxy)]propyl}pyrrolidine with an equivalent amount of 1-{[2-chloro-3-(1-naphthyloxy)]propyl}piperidine,
1-{[2-chloro-3-(1-naphthyloxy)]propyl}morpholine, or
1-{[2-chloro-3-(1-naphthyloxy)]propyl}-4-methylpiperazine, the following compounds of formula 5 in which Z is the azide radical, 1-{[1-azidomethyl)-2-(1-naphthyloxy)]ethyl}piperidine, nmr (CDCl₃) δ 1.50 (m, 6H), 2.77 (m, 4H), 3.25 (m, 1H), 3.55 (m, 2H), 4.23 (m, 2H), 6.70–8.50 (M, 7H).
1-{[1-(azidomethyl)-2-(1-naphthyloxy)]ethyl}morpholine, and
1-{[1-(azidomethyl)-2-(1-naphthyloxy)]ethyl}-4-methylpiperazine, are obtained, respectively.

Positional isomers of the latter four compounds also are isolated; for example, the positional isomer 1-{[2-azido-3-(1-naphthyloxy)]propyl}piperidine; nmr (CDCl₃) δ 1.50 (m, 6H), 2.54 (m, 6H), 4.20 (m, 3H) and 6.70–8.50 (m, 7H).

In the same manner but replacing 1-{[2-chloro-3-(1-naphthyloxy)]-propyl}pyrrolidine with an equivalent amount of 2-chloro-N-ethyl-3-(1-naphthyloxy)propylamine,
2-chloro-N-butyl-3-(1-naphthyloxy)propylamine, or
2-chloro-N,N-diisopropyl-3-(1-naphthyloxy)propylamine, the following compounds of formula 5 in which Z is the azide radical, 1-(azidomethyl)-N-ethyl-2-(1-naphthyloxy)ethylamine,
1-(azidomethyl)-N-butyl-2-(1-naphthyloxy)ethylamine, and
1-(azidomethyl)-N,N-diisopropyl-2-(1-naphthyloxy)ethylamine, are obtained, respectively.

EXAMPLE 4

β-[(1-Naphthyloxy)methyl]-1-pyrrolidineethanamine (1; Ar = 1-naphthyl, $NR^1R^2$ = 1-pyrrolidinyl and $NR^3R^4$ = $NH_2$)

A solution of 1-{[1-(azidomethyl)-2-(1-naphthyloxy)-]ethyl}-pyrrolidine (9.4 g), described in Example 3, in methanol (150 ml) is subjected to hydrogenation in the presence of platinum oxide (940 mg) at about one atmosphere at 25° C. (absorption of hydrogen is complete after 4 hours). Thereafter, the catalyst is removed by filtration and the filtrate concentrated. The residue is purified by chromatography on silica gel. Elution with diethyl ether and methanol-diethyl ether (3:17) gives the title compound, nmr (CDCl₃) δ 1.4 (2H), 1.75 (m, 4H), 2.75 and 3.05 (m, 7H), 4.3 (d,j = 5Hz, 2H) and 6.8–8.9 (n, 7H).

The hydrochloric acid addition salt (hydrochloride) of the above compound has mp 183–184° C., after recrystallization from methanol-diethyl ether.

In the same manner but replacing 1-{[1-(azidomethyl)-2-(1-naphthyloxy)]ethyl}pyrrolidine with an equivalent amount of 1-{[1-(azidomethyl)-2-(1-naphthyloxy)]ethyl}piperidine, described in Example 3, β-[(1-naphthyloxy)methyl]-1-piperidineethanamine (1; Ar = 1-naphthyl, $NR^1R^2$ = piperidino and $NR^3R^4$ = $NH_2$), nmr (CDCl₃) δ 1.52 (m, 6H), 2.40–3.30(m, 7H), 3.23 (2H), 4.22 (m, 2H) and 6.70–8.50 (m, 7H), is obtained. The hydrochloric acid addition salt (hydrochloride) of the latter compound has mp 202–208° C., after recrystallization from methanol-diethyl ether.

In the same manner but replacing 1-{[1-azidomethyl)-2-(1-naphthyloxy)]-ethyl}pyrrolidine with an equivalent amount of the positional isomer noted in Example 3, i.e., 1-{[2-azido-3-(1-naphthyloxy)]propyl}pyrrolidine α-[(1-naphthyloxy)methyl]-1-pyrrolidineethanamine(1; Ar = 1-naphthyl, $NR^1R^2$ = $NH_2$ and $NR^3R^4$ = 1-pyrrolidinyl), nmr (CDCl₃) δ 1.53 (m, 6H), 1.92 (2H), 2.47 (d, j = 6Hz + m, 6H), 3.54 (m, 1H), 4.13 (m, 2H) and 6.70–8.50 (m, 7H), is obtained.

In the same manner but replacing 1-{[1-)azidomethyl)-2-(1-naphthyloxy)]ethyl}pyrrolidine with an equivalent amount of the positional isomer noted in Example 3, i.e., 1-{[2-azido-3-(1-naphthyloxy)]propyl}piperidine, α-[(1-naphthyloxy)methyl]-1-piperidineethanamine (1; Ar = 1-naphthyl, $NR^1R^2$ = $NH_2$ and $NR^3R^4$ = piperidino), nmr (CDCl$_3$) δ 1.53 (m, 6H), 1.92 (2H), 2.47 (1d, j = 6Hz and m, 6H), 3.54 (m, 1H), 4.13 (m, 2H) and 6.70–8.50 (m, 7H) is obtained. The hydrochloric acid addition salt (dihydrochloride) of the latter compound has mp 225–230° C., after recrystallization from methanol-diethyl ether.

In the same manner but replacing 1-{[1-(azidomethyl)-2-(1-naphthyloxy)]ethyl}pyrrolidine with an equivalent amount of 1-{[1-(azidomethyl)-2-(1-naphthyloxy)]ethyl}morpholine, or
1-{[1-(azidomethyl)-2-(1-naphthyloxy)]ethyl}-4-methylpiperazine, the following compounds of formula 1

β-[(1-naphthyloxy)methyl]-4-morpholineethanamine, and
β-[(1-naphthyloxy)methyl]-4-methyl-1-piperazineethanamine, are obtained respectively.
Similarly, replacement with 1-(azidomethyl)-N-ethyl-2-(1-naphthyloxy)ethylamine,
1-(azidomethyl)-N-butyl-2-(1-naphthyloxy)ethylamine, or
1-(azidomethyl)-N,N-diisopropyl-2-(1-naphthyloxy)ethylamine, gives β-(N-ethylamino-β-[(1-naphthyloxy)methyl]ethanamine,
β-(N-butylamino)-β-[(1-naphthyloxy)methyl]ethanamine, and
β-(N,N-diisopropylamino)-β-[(1-naphthyloxy)methyl]ethanamine, respectively.

EXAMPLE 5

N-Ethyl-β-[(1-naphthyloxy)methyl]-1-piperidineethanamine (1; Ar = 1-naphthyl, $NR^1R^2$ = piperidino and $NR^3R^4$ = $NHCH_2CH_3$)

A suspension of the compound of formula 4,1-{[2-chloro-3-(1-naphthyloxy)]propyl}piperidine (15.0 g), described in Example 2, in aqueous ethylamine (30%, 60 ml) is stirred for 18 hours.

Excess ethylamine is removed by evaporation.

The mixture is extracted with diethyl ether. The ether extract is washed, dried and evaporated to dryness. The residue is subjected to chromatography using silica gel. Elution with methanol-diethyl ether (3:17) gives the title compound, mp 134°-136° C., after recrystallization from ethyl acetate-diethyl ether.

Continued elution with the same solvent gives the positional isomer, N-ethyl-α-[(1-naphthyloxy)methyl]-1-piperidineethanamine (1; Ar = 1-naphthyl, $NR^1R^2$ = $NHCH_2CH_3$ and $NR^3R^4$ = piperidino), mmr CDCl$_3$) δ 1.15 (t, J = 7,3H), 1.5 (m, 6H), 2.18 (s, 1H), 2.35–3.45 (m, 9H), 4.5 (m,2H), 6.8-8.4 (m, 7H).

In the same manner but replacing the ethylamine with isopropylamine, piperidine or morpholine, N-isopropyl-β-[(1-naphthyloxy)methyl]-1-piperidineethanamine mmr (CDCl$_3$) δ 1.12 (3, 9H), 1.5 (m, 6H), 2.08 (s, 1H), 2.85 (m, 7H), 4.25 (m, 2) and 6.8 – 8.4 (m, 7H), the corresponding hydrochloric acid addition salt (hydrochloride) of the latter compound has mp 182–184° C., after recrystallization from ethyl acetate-methanol-diethyl ether,
1-[3-(1-naphthyloxy)-2-(1-piperidinyl)propyl]piperidine, and
4-[3-(1-naphthyloxy)-2-(1-piperidinyl)propyl]morpholine, are obtained, respectively.

By following the procedure of Example 5 and using an appropriate β-chloropropylamine of formula 4 together with an appropriate amine of formula $NHR^3R^4$ in which $R^3$ is hydrogen or lower alkyl and $R^4$ is lower alkyl, then corresponding compounds of formula 1 are obtained.

For example, by using the β-chloropropylamine, 2-chloro-N,N-diisopropyl-3-(1-naphthyloxy)propylamine, described in Example 2, and piperidine, N,N-(diisopropylamine)-β-[(1-naphthyloxy)methyl]-1-piperidineethanamine, (Ar = 1-naphthyl, $NR^1R^2$ = $N[CH(CH_3)_2]_2$ and $NR^3R^4$ = piperidino), mp 48°–50° C., after recrystallization from isopropanol, is obtained. The sulfuric acid addition salt (sulfate) of the latter compound has mp 134–137° C., after recrystallization from methanol-diethyl ether.

Examples of other compounds of formula 1 prepared by following the procedure of Example 5 are illustrated in the following table.

| | STARTING MATERIALS | | PRODUCT |
|---|---|---|---|
| EXAMPLE | β-Chloropropylamine of formula 4 (Ar = 1-naphthyl and $NR^1R^2$ is as listed below | Amine of formula $NHR^3R^4$ | Compound of Formula I |
| 6 | 1-pyrrolidinyl | ethylamine | N-ethyl-β-[(1-naphthyloxy)methyl]-1-pyrrolidineethanamine |
| 7 | 1-pyrrolidinyl | piperidine | 1-[3-(-1-naphthyloxy)-2-(1-pyrrolidinyl)propyl]piperidine |
| 8 | piperidino | propylamine | N-propyl-β-[(1-naphthyloxy)methyl]-1-piperidineethanamine |
| 9 | 1-pyrrolidinyl | propylamine | N-propyl-β-[(1-naphthyloxy)methyl]-1-pyrrolidineethanamine |
| 10 | 1-pyrrolidinyl | piperidine | 1-[3-(1-naphthyloxy)-2-(1-pyrrolidinyl)propyl]piperidine |
| 11 | 4-methyl-1-piperazinyl | ethylamine | N-ethyl-β-[(1-naphthyloxy)methyl]-[1-(4-methyl-piperazine)]ethanamine |
| 12 | 4-methyl-i-piperazinyl | pyrrolidine | 1-{α[(1-naphthyloxy)methyl]-β-(1-pyrrolidinyl)ethyl}-4-methyl-piperazine |
| 13 | ethylamino | ethylamine | N-ethyl-β-(n-ethylamine)-β-[(1-naphthyloxy)methyl]-ethanamine |
| 14 | butylamino | ethylamine | N-ethyl-β-(n-butylamino)-β-[(1-naphthyloxy)methyl]-ethanamine |

-continued

| EXAMPLE | STARTING MATERIALS β-Chloropropylamine of formula 4 (Ar = 1-naphthyl and NR$^1$R$^2$ is as listed below | Amine of formula NHR$^3$R$^4$ | PRODUCT Compound of Formula I |
|---|---|---|---|
| 15 | butylamino | morpholine | 4-[3-(1-naphthyloxy)-2-(butylamino)propyl]morpholine |
| 16 | ethylamino | pyrrolidine | 1-[3-(1-naphthyloxy)-2-(ethylamino)propyl]-pyrrolidine |

We claim:

1. A compound formula 1

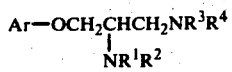

in which Ar is 1-naphthyl; R$^1$ and R$^2$ together with the nitrogen atom to which they are joined form a heterocyclic amine radical selected from the group consisting of 1-pyrrolidinyl and piperidino, and R$^3$ and R$^4$ are either the same or different selected from the group consisting of hydrogen or lower alkyl.

2. β-[(1-Naphthyloxy)methyl]-1-pyrroiidineethanamine, as claimed in claim 1.

3. The hydrochloride of the compound of claim 2.

4. β-[(1-Naphthyloxy)methyl]-1-piperidineethanamine, as claimed in claim 1.

5. The hydrochloride of the compound of claim 4.

6. N-Ethyl-β-[(1-naphthyloxy)methyl]-1-piperidineethanamine, as claimed in claim 1.

7. N-isopropyl-β-[(1-naphthyloxy)methyl]-1-piperidineethanamine, as claimed in claim 1.

8. The hydrochloride of the compound of claim 7.

9. α-[(1-Naphthyloxy)methyl]-1-pyrrolidineethanamine.

10. N-Ethyl-α-[(1-naphthyloxy)methyl]-1-piperidineethanamine.

11. A pharmaceutical composition comprising an antidepressant effective amount of a compound of formula 1 of claim 1, or a therapeutically acceptable acid addition salt thereof, and a pharmaceutically acceptable carrier.

12. A method of alleviating symptoms of depression in a mammal comprising administering to said mammal an antidepressant effective amount of a compound of formula 1 of claim 1, or a therapeutically acceptable acid addition salt thereof.

13. A pharmaceutical composition comprising an antidepressant effective amount of a compound selected from α-[(1-Naphthyloxy)methyl]-1-pyrrolidineethanamine and N-Ethyl-α-[(1-naphthyloxy)methyl]-1-piperidineethanamine, or a therapeutically acceptable acid addition salt thereof, and a pharmaceutically acceptable carrier.

14. A method of alleviating symptoms of depression in a mammal comprising administering to said mammal an antidepressant effective amount of a compound selected from α-[(1-Naphthyloxy)methyl]-1-pyrrolidineethanamine and N-Ethyl-α-[(1-naphtyloxy)methyl]-1-piperidineethanamine, or a therapeutically acceptable acid addition salt thereof.

15. A compound of formula 5

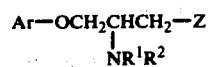

in which Ar is 1-naphthyl: R$^1$ and R$^2$ are either the same or different selected from the group consisting of hydrogen or lower alkyl, or R$^1$ and R$^2$ together with the nitrogen atom to which they are joined form a heterocyclic amine radical selected from the group consisting of 1-pyrrolidinyl, piperidino, morpholino and 4-(lower alkyl)-1-piperazinyl; and Z is the azide radical.

16. 1-{[1-Azidomethyl)-2-(1-naphthyloxy)]ethyl}pyrrolidine, as claimed in claim 15.

17. 1-{[1-Azidomethyl)-2-(1-naphthyloxy)]ethyl}piperidine, as claimed in claim 15.

18. 1-{[2-Azido-3-(1-naphthyloxy)]propyl}pyrrolidine.

19. 1-{[2-azido-3-(1-naphthyloxy)]propyl}piperidine.